US009295572B2

(12) United States Patent
Stout (10) Patent No.: US 9,295,572 B2
(45) Date of Patent: Mar. 29, 2016

(54) SHARED HAPTIC DEVICE WITH SENSORS FOR IN-SITU GESTURE CONTROLS (76) Inventor: Kelsey MacKenzie Stout, Bakersfield, CA (US)

(*) Notice: Subject to any disclaimer, the term of this patent is extended or adjusted under 35 U.S.C. 154(b) by 358 days.

(21) Appl. No.: 13/040,279

(22) Filed: Mar. 4, 2011

(65) Prior Publication Data

US 2011/0218395 A1 Sep. 8, 2011

Related U.S. Application Data (60) Provisional application No. 61/310,687, filed on Mar. 4, 2010.

(51) Int. Cl.
*A61F 5/00* (2006.01)
(52) U.S. Cl.
CPC ........................................ *A61F 5/00* (2013.01)
(58) Field of Classification Search
CPC .................. A61H 19/44; A61H 19/34; A61H 2201/0153; A61H 23/0263; A61H 19/32
USPC .............................................. 600/38; 601/46
See application file for complete search history.

(56) References Cited

U.S. PATENT DOCUMENTS

| 2004/0082831 | A1* | 4/2004 | Kobashikawa et al. | 600/38 |
| 2009/0093673 | A1* | 4/2009 | Lee | 600/38 |
| 2009/0270674 | A1* | 10/2009 | Trzecieski | 600/38 |
| 2010/0174135 | A1* | 7/2010 | Shim | 600/38 |
| 2010/0268021 | A1* | 10/2010 | Standfest et al. | 600/38 |

* cited by examiner

Primary Examiner — Christine H Matthews
(74) Attorney, Agent, or Firm — KSIP (57) ABSTRACT A vibrator sex toy is provided with touch-based sensors for an ergonomic in-situ method of controlling the operation and intensity of the vibrator. The vibrator sex toy has an internal end, an external end and a middle staging section. The staging section includes a control circuit and batteries. The internal end includes electric vibrator motors connected to the control circuit by wires. The external end includes ergonomically placed touch sensors that behave like variable resistors. The touch sensors respond to natural human gestures such as grasping, stretching, compressing and bending the external end of the sex toy with changes in resistance. The touch sensors are connected to the control circuit by wires and act as potentiometers in the control path of the vibrator motors. The user is able to vary the sensations from the motors intuitively and in-situ by manipulating the external end or applying it to a partner.

18 Claims, 4 Drawing Sheets

FLOW CHART FOR CYBERNETIC
VIBRATOR WITH IN-SITU GESTURE
CONTROLS

FIG. 5

SHARED HAPTIC DEVICE WITH SENSORS FOR IN-SITU GESTURE CONTROLS

CROSS-REFERENCE TO RELATED APPLICATION

This application claims priority under 35 U.S.C. §119(e) from U.S. Provisional Patent Application No. 61/310,687, by Stout, "Cybernetic Vibrator With Sensors For Natural Gesture Controls", filed Mar. 4, 2010, which is incorporated by reference for all purposes.

TECHNICAL FIELD

The present invention relates generally to sex toys. More particularly, the present invention relates to a sex toy with in-situ hands-free controls.

BACKGROUND INFORMATION

Vibrating sex toys, also known as "vibrators", are typically equipped with fader-style controls that allow a user to vary the intensity of an electric vibrator motor, thereby altering the sensations produced by the toy. Unfortunately, fader-type controls in a vibrator sex toy are not optimal because they are distractions from the very sensations they control. A more natural and ergonomic method of controlling a vibrator sex toy in-situ is sought.

Additionally, a sex toy is often employed by a user in conjunction with a partner. The user may apply the sex toy with a phallic or other shape to the partner. One form of such a sex toy that is employed with a partner is the "double-ended dildo", which allows a female user to mimic having a phallus to apply to a partner. Such a double-ended dildo may include vibrating motors, but, again, a fader-type control is often not useable with this form of sex toy. A fader-type control in a double-ended dildo form of sex toy is awkward and distracts from the ability to mimic having a phallus. A method of controlling this form of vibrator sex toy that simultaneously employs input by both the user and the user's partner by a user is sought.

SUMMARY

A vibrator sex toy is provided with touch-based sensors for an ergonomic method of controlling the operation and intensity of the vibrator using natural gestures. The vibrator sex toy has an internal end, an external end and a middle staging section. The staging section includes a control circuit and batteries. The internal end includes electric vibrator motors connected to the control circuit by wires. The external end includes ergonomically placed touch sensors that behave like variable resistors.

The described internal end, external end and staging section are portions of a silicone housing, with electrical components deployed between layers of silicone. Alternatively, the electrical components may be deployed in the interior of a hollow silicone housing. The housing may also be constructed of materials other than silicone.

The touch sensors may be of known types, such as pressure sensors, bend sensors, stretch sensors, compression sensors, temperature sensors, humidity sensors, galvanic skin sensors, photoresistors, accelerometers or other types of sensors. Because they are deployed just at or under the surface of the silicone housing, natural human gestures such as grasping, stretching, squeezing and bending the external end of the sex toy activate the embedded sensors. The embedded sensors respond to activation with a change in resistance to current flowing through the sensors via electrical leads. This change in resistance allows the sensors to function as variable resistors in the control path of the one or more vibrator motors.

The touch sensors are connected to the control circuit in the staging section by electrical leads. One or more sensors may be connected in series or in parallel in the control path of a motor such that input from one or more sensors changes the frequency or rhythm of a vibrator motor. Thus, touch and movement by the user and the user's partner dynamically varies the behavior of the vibrator motors in the course of manipulating the external end of the toy or applying it to a partner. Interrupting the use of the toy in order to employ a fader-style control is made unnecessary. Touches and movements that obviate the need to employ traditional fader, dial or button controls will be referred to herein as in-situ gestures.

Other methods and structures are described in the detailed description below. This summary does not purport to define the invention. The invention is defined by the claims.

DETAILED DESCRIPTION

Figure 1:
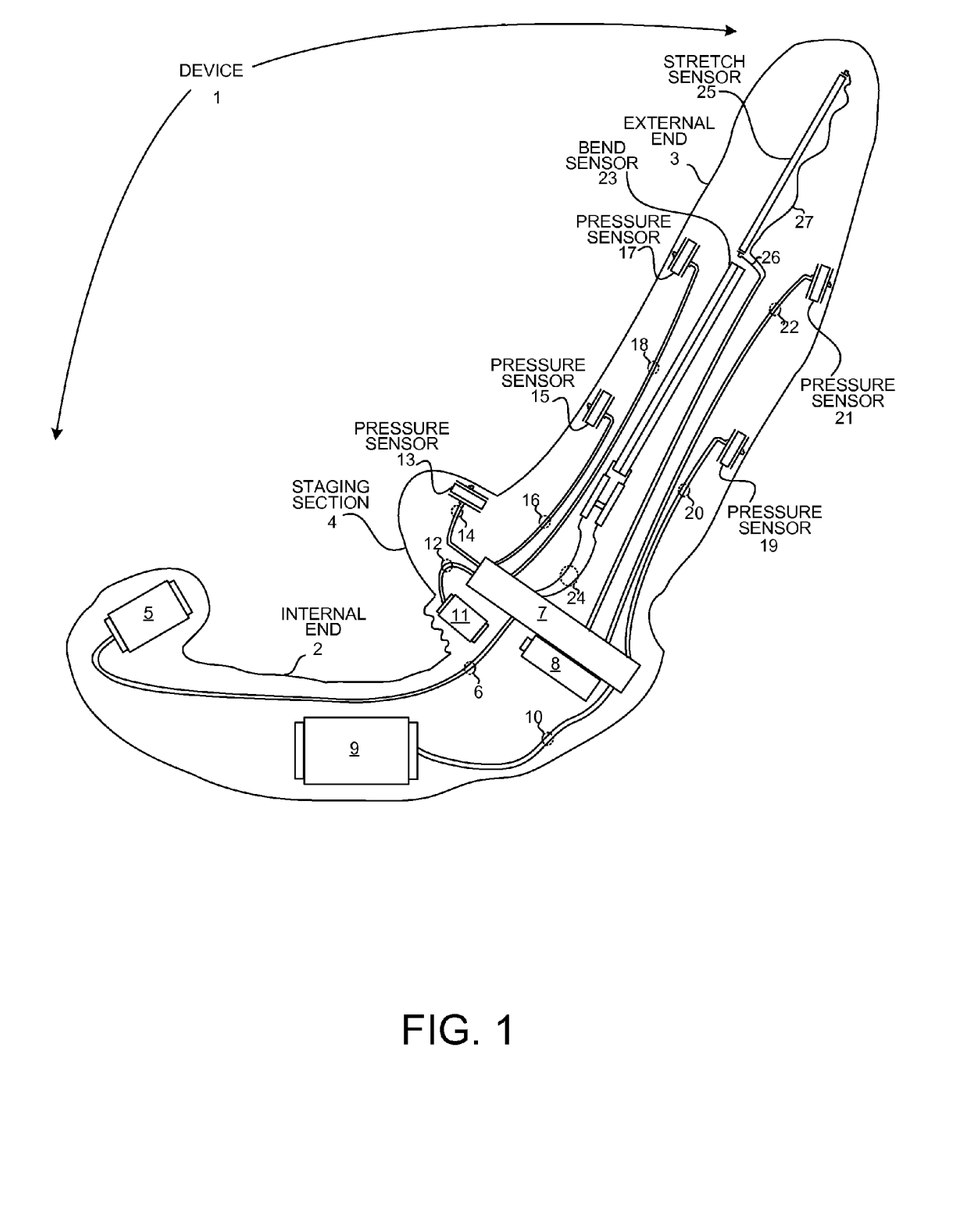
FIG. 1 is a side view of an embodiment of a cybernetic vibrator device with ergonomic sensor-based controls, in accordance with one novel aspect.

FIG. 1 is a side view of an example cybernetic vibrator device 1 with ergonomic sensor-based controls, in accordance with one novel aspect. The device 1 is made of silicone or other material such as "Cyberskin". The material of the device 1 is flexible, such that bend and stretch sensors embedded in the materials can be flexed or stretched or compressed. The material of the device 1 also ideally allows embedding of compression sensors near the surface of the material.

Device 1 includes an internal end 2, and external end 3 and a (middle) staging section 3. The internal end 2 in the example drawing is shaped to conform to a woman's genitalia, but may have another shape. In the illustrated example, the internal end 2 includes a first electric vibrator motor 5 connected by a pair of electrical leads 6 to a control circuit 7 housed in the staging section 4. A second example vibrator motor 9 connected to the control circuit 7 by a pair of electrical leads 10 is also pictured. Note that, in other embodiments, the example motors may perform functions other than vibration, such as altering the shape of the silicone body of the device 1. Motors in this example are voltage controlled motors.

A third example vibrator motor 11 is housed in the staging section 4 of the device 1 and connected to the control circuit 7 by a pair of electrical leads 12. The control circuit 7 in the staging section 4 is powered by one or more batteries 8. The control circuit 4 supplies power to the example motors 5, 9 and 11 and controls the voltages of the power supplied to each motor.

Staging Section

Housed in the staging section 4 near the surface of the silicone material is a first force sensor 13, such as a force sensing resistor. The first force sensor 13 is connected with the control circuit by a pair of electrical leads 14. Note that such a sensor may also have a third (ground) lead, which is not illustrated. Via its pair of electrical leads 14, the first force sensor 13 forms part of the control path of an example vibrating motor. In the illustrated example, the first force sensor 13 is in the control path of the first electric vibrator motor 5.

The resistance to current flowing through first force sensor 13 via leads 14 changes when force is applied to the sensor 13. Thus, when pressure is applied to the surface of the staging section 4 near the sensor 13, resistance in the control circuit for first electric vibrator motor 5 is altered. The resistance change in the control circuit produces a control signal, such as a change in voltage, that controls the speed of electric vibrator motor 5. Because the internal end 2 of the device 1 is worn inserted into the vagina with the staging section 4 forward of the pubic bone, pressure can be applied to first force sensor 13 by pressing the hips forward against a partner or hard surface rather than by a hand.

First electric vibrator motor 5 thus vibrates at varying speeds in response to ergonomic input by the user or user's partner. Such ergonomic input will be referred to here as in-situ gestures. In-situ gestures include actions taken by the user or by the user's partner in the course of using the device that can have a purpose beyond or in addition to the purpose of controlling the electrical elements of the device. As examples, users of the device may wish to change the location, shape, camber, angle of attack of the device, or change their grip on the device. In doing so, users will perform in-situ gestures such as bending, grasping, squeezing, moving, and shaking the device, as well as swiping a finger across the surface of the device, stretching the device longitudinally, and compressing the device longitudinally. Thus, natural motions and gestures by users in the course of using the device control the vibrations produced.

In-situ gestures do not have to be performed by hand. A user could perform an in-situ gesture by applying pressure to the device using, for instance, the pelvis. In-situ gestures here are contrasted with and do not include controlling a device by manipulating a traditional electrical control such as a fader, slider, dial, button or switch.

Upper Surface

Second force sensor 15 is similarly housed in the external end 3 near the upper surface of the silicone material. The second force sensor 15 is connected with the control circuit by a pair of electrical leads 16. Via its pair of electrical leads 16, the second force sensor 15 forms part of the control path of an example vibrating motor.

In the illustrated example, the second force sensor 15 is in the control path of the second electric vibrator motor 9 and pressure on the external end 3 of the device near second force sensor 15 affects the voltage supplied to second electric vibrator motor 9. Second electric vibrator motor 9 thus vibrates at varying speeds due to varying pressures on the external end 3 of the device caused by sexual activity without the need for manual input by the user or the user's partner.

Third force sensor 17 is also housed in the external end 3 near the upper surface of the silicone material. The third force sensor 17 is connected with the control circuit by a pair of electrical leads 18. Via its pair of electrical leads 18, the third force sensor 17 forms part of the control path of an example vibrating motor.

In the illustrated example, the third force sensor 17 is in the control path of the second electric vibrator motor 9. Third force sensor 17 may be disposed in series or in parallel with second force sensor 15 in this example. Pressure on the external end 3 of the device 1 near third force sensor 17 affects the voltage supplied to second electric vibrator motor 9. Second electric vibrator motor 9 thus vibrates at varying speeds due to varying pressures on the external end 3 of the device caused by sexual activity without the need for manual input by the user or the user's partner.

Lower Surface

Fourth force sensor 19 is housed in the external end 3 near the lower surface of the silicone material. The fourth force sensor 19 is connected with the control circuit by a pair of electrical leads 20. Via its pair of electrical leads 20, the fourth force sensor 19 forms part of the control path of an example vibrating motor.

In the illustrated example, the fourth force sensor 19 is in the control path of the third electric vibrator motor 11 and pressure on the external end 3 of the device near fourth force sensor 19 affects the voltage supplied to third electric vibrator motor 11. Third electric vibrator motor 11 thus vibrates at varying speeds due to varying pressures on the external end 3 of the device caused by sexual activity without the need for manual input by the user or the user's partner.

Fifth force sensor 21 is also housed in the external end 3 near the lower surface of the silicone material. The fifth force sensor 21 is connected with the control circuit by a pair of electrical leads 22. Via its pair of electrical leads 22, the fifth force sensor 21 forms part of the control path of an example vibrating motor.

In the illustrated example, the fifth force sensor 21 is in the control path of the third electric vibrator motor 11. Fifth force sensor 21 may be disposed in series or in parallel with fourth force sensor 19 in this example. Pressure on the external end 3 of the device 1 near fifth force sensor 21 affects the voltage supplied to second electric vibrator motor 11. Third electric vibrator motor 11 thus vibrates at varying speeds due to varying pressures on the external end 3 of the device caused by sexual activity without the need for manual input by the user or the user's partner.

Bend Sensors

An example bend sensor 23 is disposed longitudinally within the external end 3. The bend sensor 23 is connected with the control circuit by a pair of electrical leads 24. Via its pair of electrical leads 24, the bend sensor 23 forms part of the control path of an example vibrating motor. In the illustrated example, the first force sensor 13 is in the control path of the first electric vibrator motor 5.

The resistance to current flowing through bend sensor 23 via leads 24 changes when force is applied to the bend sensor 23. Thus, when external end 3 is bent upwards or downwards, resistance in the control circuit for first electric vibrator motor 5 is altered such that the voltage supplied to first electric vibrator motor 5 is also altered. Because the external end 3 of the device 1 is flexible and undergoes constant changes in bend angle due to sexual activity, first electric vibrator motor 5 vibrates at varying speeds in response to the motion of the user or the user's partner without the need for manual input.

Strain Sensor

An example strain sensor 25 (also known as a stretch sensor) is disposed longitudinally within the external end 3. the strain sensor 25 is connected with the control circuit by a pair of electrical leads 26 and 27. Via its pair of electrical leads 26 and 27, the strain sensor 25 forms part of the control path of an example vibrating motor. In the illustrated example, the strain sensor 25 is in the control path of the third electric vibrator motor 11.

The resistance to current flowing through strain sensor 25 via leads 26 and 27 changes when the strain sensor 23 is stretched or compressed longitudinally. Thus, when external end 3 is stretched or compressed longitudinally, resistance in the control circuit for third electric vibrator motor 11 is altered such that the voltage supplied to third electric vibrator motor 11 is also altered. Because the external end 3 of the device 1 is flexible and undergoes stretching and longitudinal compression due to sexual activity, third electric vibrator motor 11 vibrates at varying speeds in response to the in-situ gestures of the user or the user's partner without the need for manual input.

Reversed Embodiment

Figure 2:
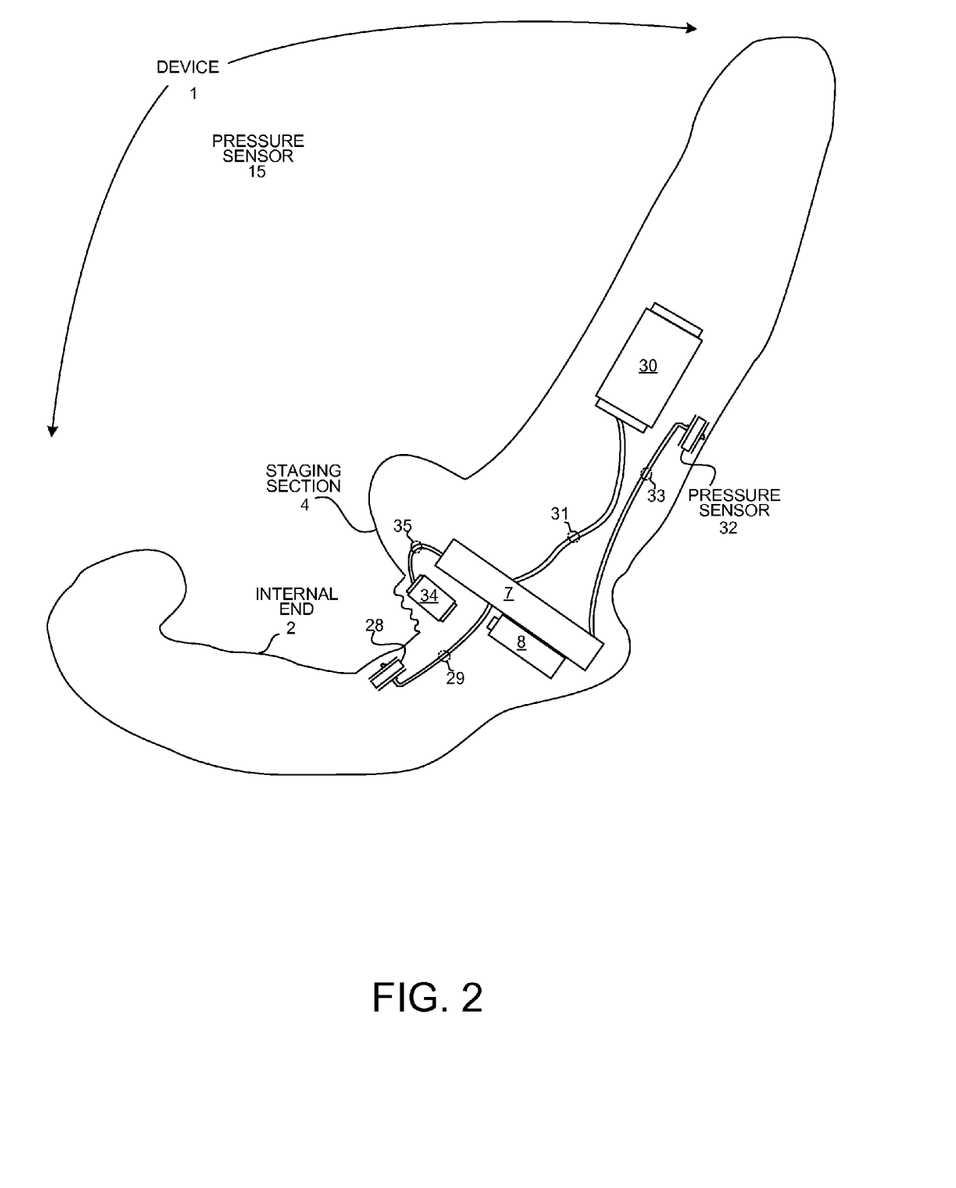
FIG. 2 is a side view of a second embodiment of a cybernetic vibrator device with reversed ergonomic sensor-based controls, in accordance with another novel aspect.

FIG. 2 is a side view of a second embodiment of a cybernetic vibrator device with reversed ergonomic sensor-based controls, in accordance with another novel aspect. In FIG. 2, touch sensors and their associated motors are disposed in either end of the device 1, such that the user and the user's partner may have simultaneous affects on touch sensors, each effectively controlling a vibrator motor sensed by the other.

Device 1 includes an internal end 2, and external end 3 and a (middle) staging section 3. The internal end 2 in the example drawing is shaped to conform to a woman's genitalia, but may have another shape. In the illustrated example, the internal end 2 includes a first force sensor 28 connected by a pair of electrical leads 29 to a control circuit 7 housed in the staging section 4.

A first example vibrator motor 30 is housed in the external end 3 of the device 1 and connected to the control circuit 7 by a pair of electrical leads 31. The control circuit 7 in the staging section 4 is powered by one or more batteries 8. The control circuit 4 supplies power to the example motors 30 and 34 and controls the voltages of the power supplied to each motor.

Via its pair of electrical leads 29, the first force sensor 28 forms part of the control path of first electric vibrator motor 5. Because the first force sensor 28 is located within the portion of device 1 which is disposed within the vagina of the user, muscular contractions of the vagina can be used to control first electric vibrator motor 5. Thus, sensations perceived by the user's partner vary in response to the natural motion of the user without the need for manual input.

A second force sensor 32 disposed within the external end 3 of the device 1 similarly controls a second example vibrator motor 34. Second vibrator motor 34 is disposed such that its vibrations are perceived by the user, and second force sensor 32 is disposed such that it is activated by natural gestures by the user's partner, as is explained above in regard to FIG. 1.

Note that various other arrangements of sensors and sensor-controlled devices can be made. The sensors may be of known types such as pressure sensors, bend sensors, stretch sensors, strain sensors, compression sensors, temperature sensors, humidity sensors, galvanic skin sensors, photoresistors, capacitive touch sensors, resistive touch sensors, accelerometers or other types of sensors. A stretch sensor, bend sensor, or other type of sensor can be disposed in the internal end 2 of the device 1 for activation by muscle contractions. Internal sensors can be connected so as to control internal vibrator motors, and external sensors can be connected so as to control external vibrator motors. Devices other than vibrator motors, such as actuators and LED lights, can also be controlled using the described methods. A microprocessor and memory can be employed to produce motor or device control signals in response to various combinations or patterns of gestures applied to the various sensors.

Example Circuit

Figure 3:
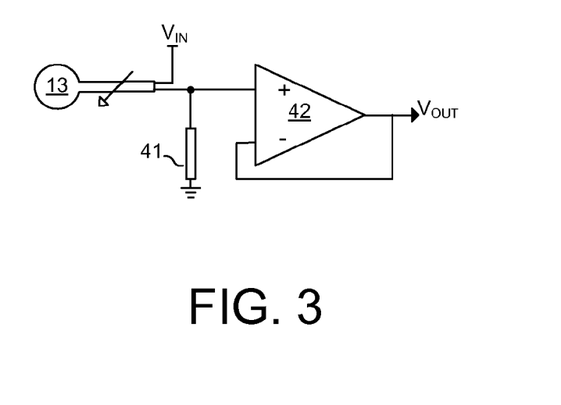
FIG. 3 is an example circuit diagram showing a force sensor 13 in the control path of a DC vibrator motor 5.

FIG. 3 is an example circuit diagram showing a force sensor 13 in the control path of a DC vibrator motor 5. Force sensor 13 is a force sensitive resistor (FSR) with, in this example, a resistance at rest of 10,000 ohms. FSR 13 is disposed in a voltage divider arrangement with a second resistor 41 which also has a resistance of 10,000 ohms. Pressure is applied to the FSR 13 when the user of the device or user's partner grasps, pulls or squeezes the device 1 housing surface near where the FSR 13 is situated.

As increasing pressure from the grasping gesture is translated through the flexible surface of the device 1 to the force sensitive portion of the FSR 13 (indicated by the rounded portion of item 13 in FIG. 3), the resistance of FSR 13 decreases from its maximum of 10,000 ohms. This allows an increased level of $V_{IN}$ to reach the op-amp 42 via the voltage divider formed by FSR 13 and resistor 41. The output of the op-amp 42 can be output to a microprocessor for voltage polling, or output to a pulse width modulation (PWM) chip for driving the motor 5 via a MOSFET.

Figure 4:
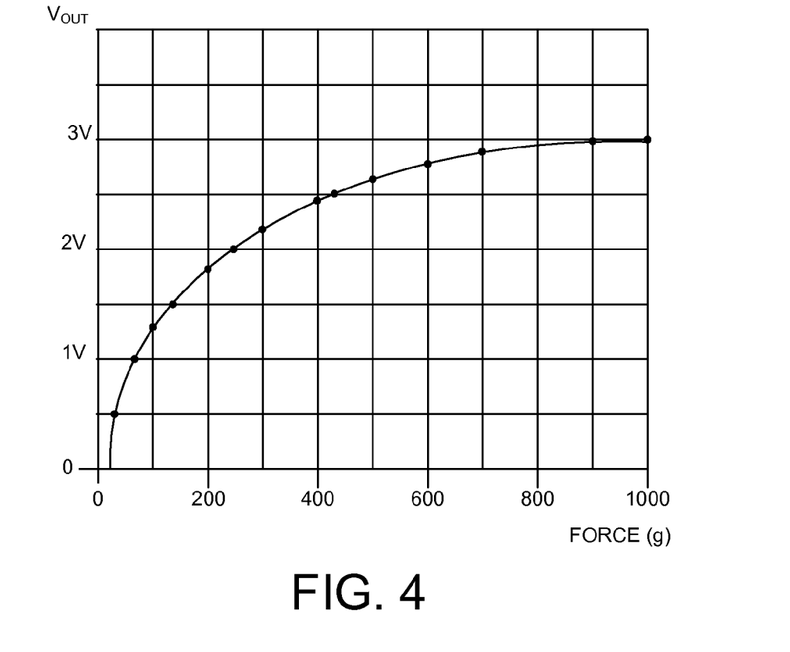
FIG. 4 is a graph showing the voltage curve through a touch sensor as touch pressure is changed.

In this example, $V_{IN}$ is three volts provided by a pair of 1.5 volt batteries 8. The resistance of example FSR 13 drops to near zero at a force of one kilogram. FIG. 4 is a graph showing the voltage curve through the voltage divider as pressure is changed. Note that this curve will be affected by the placement of the sensor and the material used for the device 1 housing. Fine tuning of the voltage curve can be done by selecting a different resistance for the second resistor 41.

Figure 5:
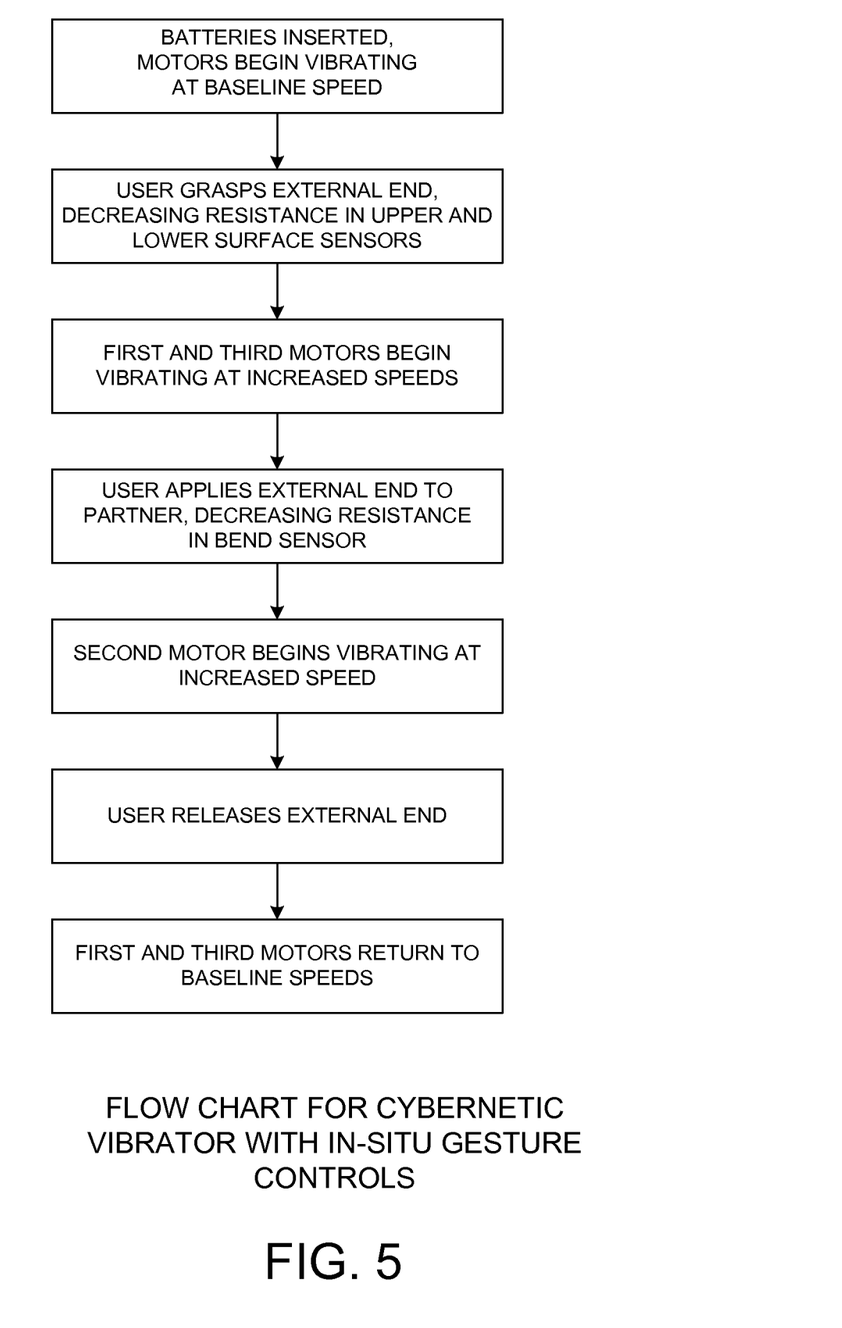
FIG. 5 is a flowchart showing the changes in actuated motor operation in accordance with natural gestures by the user and user's partner.

FIG. 5 is a flowchart showing the changes in actuated motor operation in accordance some example natural gestures by the user and user's partner.

Note that though the touch sensors in the above examples can be thought of as rheostats for controlling the voltage of power supplied to DC motors, other embodiments may employ the touch sensors as motor controls using different methods. Characteristics of the sensors other than changes in resistance, such as instant voltages, may be used. Touch sensors may be in the control path of a DC motor that is controlled via pulse-width modulation (PWM). In another embodiment, the device may employ a microprocessor that polls the electrical characteristics of touch sensors and in response controls DC motors according to programmed responses. Such an embodiment employing a microprocessor may also include a digital interface, such as a USB port, located in the staging section 4. A user could employ the digital interface to modify the programmed responses of the microprocessor.

Note also that the depicted shape of the device is not the only possible shape. The device may, for example, take a traditional cylindrical shape. The housing may be made entirely or only partially of flexible material.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. An apparatus comprising:

a housing of flexible material, said housing comprising: an external extremity having a tip, an internal extremity having a tip, and a middle portion,
  said external extremity having a proximal end contiguous to said middle portion, a distal end being the tip of the external extremity furthest from said middle portion and a proximo-distal axis extending through the center of the external extremity from its proximal end to its distal end,
  said external extremity having a dorsal side and a ventral side, said external extremity having a dorsal curve when at rest,
    said internal extremity having a proximal end contiguous to said middle portion, a distal end being the tip of the internal extremity furthest from said middle portion and a proximo-distal axis extending through the center of the internal extremity from its proximal end to its distal end,
    said internal extremity and external extremity being disposed such that a lengthwise axis runs from the distal tip of the internal extremity, through the proximo-distal axis of the internal extremity, through the middle portion of the apparatus housing, through the proximo-distal axis of the external extremity, to the distal tip of the external extremity,
    a control circuit configured to recognize a first sensor output control signal and produce a first motor input control signal in response,
  a first sensor that produces the first sensor output control signal in response to at least a first in-situ gesture, said first sensor having a proximal and nearest the middle portion of the housing, a distal end situated nearest the distal end of the external extremity and a proximo-distal axis extending through the center of the first sensor from its proximal end to its distal end,
  said first sensor being disposed within the external extremity of the apparatus such that its proximo-distal axis is parallel to the proximo-distal axis of the external extremity,
    said first sensor being connected to said control circuit by a first lead, and a first motor having a speed, wherein the speed of said first motor varies in response to said first motor input control signal, wherein said apparatus is a sex toy.

2. The apparatus of claim 1, said first sensor being disposed within the external extremity of the apparatus such that its proximo-distal axis is contiguous with the proximo-distal axis of the external extremity.

3. The apparatus of claim 1,
  said external extremity having a degree of dorsal curvature,
  said internal extremity having a degree of dorsal curvature,
  said first in-situ gesture being taken from the group consisting of:
  increasing the degree of dorsal curvature of said external extremity,
  increasing the degree of dorsal curvature of said internal extremity,
  decreasing the degree of dorsal curvature of said external extremity,
  decreasing the degree of dorsal curvature of said internal extremity,
  stretching parallel to the proximo-distal axis of said external extremity,
  compressing parallel to the proximo-distal axis of said external extremity such that said external extremity is shortened,
  performing tubular compression perpendicular to the proximo-distal axis of said external extremity; and
  performing tubular compression perpendicular to the proximo-distal axis of said internal extremity.

4. The apparatus of claim 1,
  wherein said apparatus is a double-ended dildo sex toy.

5. The apparatus of claim 1,
  wherein said first sensor is taken from the group comprising:
  a set of at least two force sensors disposed in a linear array;
  a bend sensor;
  and
  a stretch sensor.

6. The apparatus of claim 1,
  also comprising:
  a second motor having a speed, wherein the speed of said second motor varies in response to said first motor input control signal, said first motor being located in said internal extremity and said second motor being located in said external extremity.

7. The apparatus of claim 1,
  also comprising:
  a second sensor having a proximal end nearest the middle portion of the housing, a distal end situated nearest the distal end of the external extremity and a proximo-distal axis extending through the center of the first sensor from its proximal end to its distal end,
    said second sensor being disposed within the external extremity of the apparatus such that its proximo-distal axis is parallel to the proximo-distal axis of the internal extremity,
    said second sensor being a bend sensor; and
    said first sensor being either a bend sensor or a stretch sensor.

8. The apparatus of claim 1,
  said external extremity of the apparatus housing having a dorsal side and a ventral side,
    said middle portion of the apparatus housing comprising a staging section,
    said staging section containing a pubic bone sensor adjacent the dorsal side of the external extremity which produces a pubic bone sensor output control signal in response to a hip-press in-situ gesture,
    said pubic bone sensor being disposed such that it senses a hip-press in-situ gesture as force directed toward said staging section substantially parallel to the proximo-distal axis of said external extremity.

9. The apparatus of claim 1,
  also comprising:
  a second sensor that produces a second sensor output control signal in response to a second in-situ gesture,
    said second sensor having a proximal end nearest the middle portion of the housing, a distal end situated nearest the distal end of the external extremity and a proximo-distal axis extending through the center of the second sensor from its proximal end to its distal end,
    said second sensor being disposed within the external extremity of the apparatus such that its proximo-distal axis is parallel to the proximo-distal axis of the external extremity,
    said second sensor being connected to said control circuit by a second lead.

10. The apparatus of claim 9,
  said control circuit being located in said middle portion of the apparatus house,
  said first sensor being a bend sensor; and said second sensor being a stretch sensor.

11. The apparatus of claim 1, also comprising:
a stretch sensor that produces a second sensor output control signal in response to a second in-situ gesture,
said stretch sensor having a proximal end nearest the middle portion of the housing, having a distal end situated nearest the distal end of the external extremity and having a proximo-distal axis extending through the center of the stretch sensor from its proximal end to its distal end,
said stretch sensor being disposed within the external extremity of the apparatus such that it is held partially stretched when at rest and such that its proximo-distal axis is parallel to the proximo-distal axis of the external extremity,
said stretch sensor being connected to said control circuit by a second lead,
said external extremity of the apparatus housing having a dorsal side and a ventral side,
said middle portion of the apparatus housing comprising a staging section,
said staging section containing a pubic bone sensor adjacent the dorsal side of the external extremity that produces a pubic bone sensor output control signal in response to a hip-press in-situ gesture,
said pubic bone sensor being disposed such that it senses a hip-press in-situ gesture directed toward said staging section substantially parallel to the proximo-distal axis of said external extremity; and
said first sensor being a bend sensor.

12. The apparatus of claim 11,
said control circuit being configured to also recognize a second sensor output control signal and produce a second motor input control signal in response, and to recognize the pubic bone sensor output control signal and produce a third motor input control signal in response; and
said first motor having a rhythm, wherein the rhythm of said first motor varies in response to said second motor input control signal and the speed of said first motor varies in response to said third motor input control signal.

13. The apparatus of claim 1, also comprising:
a second sensor that produces a second sensor output control signal in response to a second in-situ gesture,
said second sensor having a proximal end nearest the middle portion of the housing, having a distal end situated nearest the distal end of the external extremity and having a proximo-distal axis extending through the center of the second sensor from its proximal end to its distal end,
said second sensor being disposed within the external extremity of the apparatus such that its proximo-distal axis is parallel to the proximo-distal axis of the external extremity,
said second sensor being connected to said control circuit by a second lead,
said control circuit being configured to also recognize a second sensor output control signal and produce a second motor input control signal in response,
said apparatus further comprising a second motor having a speed, wherein the speed of said second motor varies in response to said second motor input control signal; and
said first motor being connected to said control circuit by a first motor lead and said second motor being connected to said control circuit by a second motor lead.

14. The apparatus of claim 13, said first sensor being a stretch sensor and said second sensor being a bend sensor.

15. An apparatus comprising:
a housing of flexible material, said housing comprising an external extremity having a tip, an internal extremity having a tip, and a middle portion,
said external extremity having a proximal end contiguous to said middle portion, a distal end being the tip of the external extremity furthest from said middle portion and a proximo-distal axis extending through the center of the external extremity from its proximal end to its distal end,
said internal extremity having a proximal end contiguous to said middle portion, a distal end being the tip of the internal extremity furthest from said middle portion and a proximo-distal axis extending through the center of the internal extremity from its proximal end to its distal end,
a first sensor that produces a first sensor output control signal in response to a first in-situ gesture,
said first sensor having a proximal end nearest the middle portion of the housing, a distal end situated nearest the distal end of the external extremity and a proximo-distal axis extending through the center of the first sensor from its proximal end to its distal end,
said first sensor being disposed within the external extremity of the apparatus such that its proximo-distal axis is parallel to the proximo-distal axis of the external extremity,
a second sensor that produces a second sensor output control signal in response to a second in-situ gesture,
said second sensor having a proximal end nearest the middle portion of the housing, a distal end situated nearest the distal end of the external extremity and a proximo-distal axis extending through the center of the second sensor from its proximal end to its distal end,
said second sensor being disposed within the external extremity of the apparatus such that its proximo-distal axis is parallel to the proximo-distal axis of the external extremity,
the apparatus also comprising a control circuit configured to produce a first motor input control signal in response to said first sensor output control signal and to produce a second motor input control signal in response to said second sensor output control signal,
said first sensor being connected to said control circuit by a first sensor lead and said second sensor being connected to said control circuit by a second sensor lead,
the apparatus also comprising a first motor having a speed, disposed within the internal extremity of the apparatus housing, wherein the speed of said first motor varies in response to said first motor input control signal,
said middle portion of the housing comprising a staging section, said staging section containing a second motor having a speed, wherein the speed of said second motor varies in response to said second motor input control signal,
said first motor being connected to said control circuit by a first motor lead and said second motor being connected to said control circuit by a second motor lead,
said external extremity having a dorsal side and a ventral side, said external extremity having a degree of dorsal curvature at rest, said first sensor being a bend sensor and said first in-situ gesture being one of either increasing the degree of dorsal curvature of said external extremity or decreasing the degree of dorsal curvature of said external extremity; and said second sensor being a stretch sensor and said second in-situ gesture being one of either stretching parallel to the proximo-distal axis of said external extremity or compressing parallel to the proximo-distal axis of said external extremity such that said external extremity is shortened, said apparatus being a double-ended dildo sex toy.

16. The apparatus of claim 15, the internal extremity of the apparatus and the staging section of the middle portion of the apparatus housing being configured so as to facilitate wearing of the apparatus with the internal extremity inserted into the vagina of a first user, said staging section containing a pubic bone sensor, adjacent the pubic bone of said first user on one side of said pubic bone sensor and adjacent the dorsal side of the external extremity of the apparatus on the opposite side of said pubic bone sensor, that produces a pubic bone sensor output control signal in response to a hip-press in-situ gesture performed by said first user, said pubic bone sensor being disposed such that it senses force direction toward said staging section substantially parallel to the proximo-distal axis of said external extremity, said external extremity being arranged such that said first in-situ gesture is one of either increasing the degree of dorsal curvature of said external extremity performed by a second user simultaneously with said hip-press in-situ gesture or decreasing the degree of dorsal curvature of said external extremity performed by a second user simultaneously with said hip-press in-situ gesture.

17. A method comprising:

sending, in response to a first in-situ gesture, a first sensor output control signal having characteristics to a control circuit from a first sensor, said first sensor being situated on or within a first extremity of a sex toy device having a motor, a control circuit with a memory, the first extremity having a tip, a second extremity, and a middle portion, said first extremity having a proximal end contiguous to said middle portion, a distal end being the tip of the first extremity furthest from said middle portion and a proximo-distal axis extending through the center of the first extremity from its proximal end to its distal end, said first sensor having a proximal end nearest the middle portion of the device, a distal end situated nearest the distal end of the first extremity and a proximo-distal axis extending through the center of the first sensor from its proximal end to its distal end, said first sensor being disposed such that its proximo-distal axis is parallel to the proximo-distal axis of the first extremity, sending, in response to a second in-situ gesture, a second sensor output control signal having characteristics to the control circuit from said first sensor, storing, in said memory, the characteristics of said first sensor output control signal, storing, in said memory, the characteristics of said second sensor output control signal, determining, in response to said steps of storing, a first output motor control signal; and sending said first output motor control signal to said motor.

18. The method of claim 17, further comprising:

sending, in response to a third in-situ gesture, a third sensor output control signal having characteristics to the control circuit from a second sensor, said second sensor being situated on or within the first extremity of said device, said second sensor having a proximal end nearest the middle portion of the device, a distal end situated nearest the distal end of the first extremity and a proximo-distal axis extending through the center of the second sensor from its proximal end to its distal end, said second sensor being disposed such that its proximo-distal axis is parallel to the proximo-distal axis of the first extremity, sending, in response to a fourth in-situ gesture, a fourth sensor output control signal having characteristics to the control circuit from said second sensor, storing, in said memory, the characteristics of said third sensor output control signal, storing, in said memory, the characteristics of said fourth sensor output control signal, determining, in response to said pattern, a first pattern of output motor control signals; and sending said first pattern of output motor control signals to said motor.

* * * * *